United States Patent [19]

Boyle et al.

[11] Patent Number: 4,910,212

[45] Date of Patent: Mar. 20, 1990

[54] HETEROCYCLIC COMPOUNDS

[75] Inventors: Francis T. Boyle, Congleton; Zbigniew S. Matusiak, Cheshire; Brian S. Tait, MacClesfield, all of England

[73] Assignee: Imperial Chemical Industries PLC, London, England

[21] Appl. No.: 155,803

[22] Filed: Feb. 16, 1988

[30] Foreign Application Priority Data

Mar. 5, 1987 [GB] United Kingdom ............... 8705174

[51] Int. Cl.$^4$ ................ C07D 233/58; C07D 249/08; A61K 31/41; A61K 31/415

[52] U.S. Cl. ..................... 514/383; 514/398; 514/399; 514/400; 548/262.2; 548/335; 548/341; 548/342

[58] Field of Search ............ 548/262, 335, 341, 342, 548/269; 514/383, 398, 399, 400

[56] References Cited

U.S. PATENT DOCUMENTS

| | | | |
|---|---|---|---|
| 4,503,062 | 3/1985 | Gravestock | 514/383 |
| 4,659,730 | 4/1987 | Hirsch et al. | 514/396 |
| 4,737,508 | 4/1988 | Lovey et al. | 514/383 |
| 4,755,526 | 7/1988 | Hirsch et al. | 514/399 |
| 4,757,082 | 7/1988 | Hirsch et al. | 514/396 |

FOREIGN PATENT DOCUMENTS 163416  4/1985  European Pat. Off. .
160508  6/1985  European Pat. Off. .
166509  2/1986  European Pat. Off. .
124369  12/1988  European Pat. Off. .

*Primary Examiner*—Richard L. Raymond
*Assistant Examiner*—Peter G. O'Sullivan
*Attorney, Agent, or Firm*—Cushman, Darby & Cushman

[57] ABSTRACT

A heterocyclic compound of the formula I, as shown hereafter in these claims in which n is 0 or 1; A is a 1-4C alkylene radical which may optionally bear one or more 1-4C alkyl substituents; $R^1$ and $R^2$, which may be the same or different, are each a hydrogen or halogen atom, an amino, carbamoyl, cyano, hydroxy, nitro or sulphamoyl radical, a 1-6C alkyl, halogenoalkyl, alkoxy, halogenoalkoxy, alkylamino, alkylcarbamoyl or alkylsulphamoyl radical, a di(1-6C alkyl)-amino, di(1-6C alkyl)carbamoyl or di(1-6C alkyl)sulphamoyl radical, or a 2-7C alkoxycarbonyl radical; m is an integer of 1 to 5, $R^3$ is a hydrogen or halogen atom or a 1-6C alkyl or halogenoalkyl radical; and $R^4$ is a 5-membered aromatic ring heterocyclyl radical containing 2 or 3 nitrogen atoms, or a 6-membered aromatic ring heterocyclyl radical containing 1 or 2 nitrogen atoms, which heterocyclyl radical may bear a 1-6C alkyl substituent; and for those compounds which contain a basic nitrogen atom, the pharmaceutically acceptable acid addition salts thereof together with processes of manufacture and pharmaceutical and veterinary compositions thereof.

10 Claims, No Drawings

HETEROCYCLIC COMPOUNDS

This invention relates to heterocyclic compounds, and in particular it relates to certain heterocyclic compounds which are useful as inhibitors of the enzyme, aromatase.

Aromatase is an enzyme which effects aromatisation of ring A in the metabolic formation of various steroid hormones. Various cancers, for example breast cancer, are dependent upon cirulating steroid hormones which have an aromatic ring A. Such cancers can be treated by removing the source of ring A aromatised steroid hormones, for example by the combination of oophorectomy and adrenalectomy. An alternative way of obtaining the same effect is by administering a chemical compound which inhibits the aromatisation of the steroid ring A, and the compounds of the invention are useful for this purpose.

According to the invention there is provided a heterocyclic compound of the formula I, shown hereafter, in which n is 0 or 1; A is a 1-4C alkylene radical which may optionally bear one or more 1-4C alkyl substituents; $R^1$ and $R^2$, which may be the same or different, are each a hydrogen or halogen atom, an amino, carbamoyl, cyano, hydroxy, nitro or sulphamoyl radical, a 1-6C alkyl, halogenalkyl, alkoxy, halogenoalkoxy, alkylamino, alkylcarbamoyl or alkylsulphamoyl radical, a di(1-6C alkyl)-amino, di(1-6C alkyl)carbamoyl or di(1-6C alkyl)sulphamoyl radical, or a 2-7C alkoxycarbonyl radical; m is an integer of 1 to 5, $R^3$ is a hydrogen or halogen atom or a 1-6C alkyl or halogenalkyl radical; and $R^4$ is a 5-membered aromatic ring heterocyclyl radical containing 2 or 3 nitrogen atoms, or a 6-membered aromatic ring heterocyclyl radical containing 1 or 2 nitrogen atoms, which heterocyclyl radical may bear a 1-6C alkyl substituent; and for those compounds which contain a basic nitrogen atom, the pharmaceutically acceptable acid addition salts thereof.

It is to be understood that when m is 2 to 5, the substituents $R^2$ may be the same or different.

A suitable value for A when it is an unsubstituted alkylene radical is a methylene, ethylene, trimethylene or tetramethylene radical, and a suitable value for A when it is an alkylene radical bearing one or more 1-4C alkyl substituents is, for example, an ethylidene, propylidene, butylidene, pentylidene, 1-methylethylidene, 1-methylbutylidene, 1-ethylethylidine, 1- or 2-methylethylene, 1- or 2-ethylethylene, 1,2-dimethylethylene, 1-, 2- or 3-methyltrimethylene, 1,2-, 1,3- or 2,3-dimethyltrimethylene, 1-, 2-, 3- or 4-methyltetramethylene or 1,2-, 1,3-, 1,4-, 2,3-, 2,4- or 3,4-dimethyltetramethylene radical.

A suitable value for $R^1$, $R^2$ or $R^3$, when any of them is a halogen atom, is for example a chlorine, fluorine, bromine or iodine atom, preferably a chlorine or fluorine atom.

A suitable value for $R^1$, $R^2$ or $R^3$, when any of them is an alkyl radical, is, for example, a methyl, ethyl, propyl, isopropyl, butyl, isobutyl, sec-butyl, tert-butyl, pentyl or hexyl radical.

A suitable value for $R^1$, $R^2$ or $R^3$, when any of them is a halogenoalkyl radical, is, for example, a halogenoalkyl radical, for example a fluoromethyl, dichloromethyl, difluoromethyl, trichloromethyl, trifluoromethyl, 2-chloroethyl, 2-fluoroethyl, 2,2,2-trichloroethyl, 2,2,2-trifluoroethyl, 1,1,2-tetrafluoroethyl, 3,3,3-trifluoropropyl, 2,2,3,3-tetrafluoro-propyl, perfluoropropyl or 4,4,4-trifluorobutyl radical.

A suitable value for $R^1$ or $R^2$, when either is an alkoxy radical, is, for example, a methoxy, ethoxy, propoxy, isopropoxy, butoxy, isobutoxy, sec-butoxy, tert-butoxy, pentyloxy or hexyloxy radical.

A suitable value for $R^1$ or $R^2$, when either is a halogenalkoxy radical, is, for example, a fluoromethoxy, difluoromethoxy, trifluoromethoxy, 2-fluoroethoxy, 2,2-difluoroethoxy, 2,2,2-trifluoroethoxy, 1,1,2-trifluoroethoxy 2,2,3,3-tetrafluoropropoxy or 1-methyl-2,2,2-trifluoroethoxy radical.

A suitable value for $R^1$ or $R^2$, when either is an alkylamino or dialkylamino radical, is, for example, a methylamino, ethylamino, propylamino, isopropylamino, butylamino, isobutylamino, pentylamino, hexylamino, dimethylamino, diethylamino, ethylmethylamino, dipropylamino, methylpropylamino or dihexylamino radical.

A suitable value for $R^1$ or $R^2$, when either is an alkylcarbamoyl or dialkylcarbamoyl radical, is, for example, a methylcarbamoyl, ethylcarbamoyl, propylcarbamoyl, isopropylcarbamoyl, hexylcarbamoyl, dimethylcarbamoyl, diethylcarbamoyl, ethylmethylcarbamoyl, dipropylcarbamoyl, methylpropylcarbamoyl or dihexylcarbamoyl radical.

A suitable value for $R^1$ or $R^2$, when either is an alkylsulphamoyl or dialkylsulphamoyl radical, is, for example, a methylsulphamoyl, ethylsulphamoyl, propylsulphamoyl, hexylsulphamoyl, dimethylsulphamoyl, diethylsulphamoyl, ethylmethylsulphamoyl, dipropylsulphamoyl or dihexylsulphamoyl radical.

A suitable value for $R^1$ or $R^2$, when either is an alkoxycarbonyl radical, is, for example, a methoxycarbonyl, ethoxycarbonyl, propoxycarbonyl, isopropoxycarbonyl or hexyloxycarbonyl radical.

n is preferably 1.

When n is 1, the substituent $R^1$ is preferably in the 6-position of the tetrahydronaphthalene ring system.

m is preferably 1 or 2. When m is 1, $R^2$ is preferably in the 4-position of the phenyl ring, and when m is 2, one of the substituents is preferably in the 4-position of the phenyl ring, and the other is in the 2- or 3-position, preferably the 2-position.

A suitable value for $R^4$ when it is a 5-membered ring heterocyclcyl radical containing 2 or 3 nitrogen atom is, for example, a 1H-1,2,4-triazolyl or 1H-imidazolyl radical, and a suitable value when it is a 6-membered ring heterocyclyl radical is, for example, a pyridyl or pyrimidinyl radical. Preferred such heterocyclyl radicals are 1H-1,2,4-triazol-1-yl, 1H-imidazol-1-yl, 3-pyridyl and 5-pyrimidinyl radicals. A suitable alkyl substituent in such a heterocyclic radical is, for example, a methyl, ethyl or hexyl radical, and a particular substituted such heterocyclic radical is, for example, a 4-methyl- or 5-methyl-1H-imidazol-1-yl radical.

Suitable pharmaceutically acceptable acid-addition salts of compounds of the invention which possess a basic nitrogen atom are, for example, the hydrochloride, nitrate, sulphate, acetate and phosphate.

A preferred group of compounds of the invention comprises those compounds wherein n is 1, A is a methylene, ethylene or trimethylene radical, $R^1$ and $R^2$, which may be the same or different, are each a chlorine or fluorine atom, or a carbamoyl, cyano, hydroxy, methoxy, trifluoromethyl or trifluoromethoxy radical, m is 1 or 2, $R^3$ is a hydrogen atom or a methyl radical, and $R^4$ is a 1H-1,2,4-triazol-1-yl, 1H-imidazol-1-yl, 4-methyl-1H-imidazol-1-yl, 5-methyl-1H-imidazol-1-yl, 3-pyridyl or 5-pyrimidinyl radical.

A more preferred group of compounds of the invention comprises those compounds wherein n is 1, A is a methylene, ethylene or trimethylene radical, $R^1$ and $R^2$, which may be the same or different, are each a chlorine or fluorine atom, or a cyano, hydroxy or methoxy, radical, m is 1 or 2, $R^3$ is a hydrogen atom or a methyl radical, and $R^4$ is a 1H-1,2,4-triazol-1-yl, 1H-imidazol-1-yl, 4-methyl-1H-imidazol-1-yl, or 5-methyl-1H-imidazol-1-yl radical. Especially preferred within this group are those compounds wherein m is 1, and the substituent $R^2$ is in the 4-position of the phenyl ring.

A particularly preferred group of compounds of the invention comprises those compounds wherein n is 1, A is a methylene radical, m is 1 or 2, one of $R^1$ and $R^2$ is a cyano radical, and the other or others of $R^1$ and $R^2$ is a chlorine or fluorine atom or a cyano radical. Especially preferred within this group are those compounds wherein m is 1 and $R^1$ and $R^2$ are selected from fluorine atoms and cyano radicals.

It is to be understood that the ring carbon atoms bearing the substituents $R^4A$ and $R^3$ are asymmetrically substituted, and that one or more carbon atoms of the alkylene radical A may also be asymmetrically unsubstituted, so that the compounds of the invention will exist in a number of different optical forms. It is a matter of common general knowledge how such different optical forms may be synthesised or separated, and their aromatase inhibitory properties determined.

Particular preferred compounds of the invention are (1R*,2R*)-6-fluoro-2-(4-fluorophenyl)-1,2,3,4-tetrahydro-1-(1H-1,2,4-triazol-1-ylmethyl)naphthalene, (1R*,2R*)-6-fluoro-2-(4-fluorophenyl)-1,2,3,4-tetrahydro-1-(1H-imidazolylmethyl)-naphthalene, (1R*,2R*)- and (1R*,2S*)-2-(4-fluorophenyl)-1,2,3,4-tetrahyro-1-(1H-1,2,4-triazol-1-ylmethyl)naphthalene-6-carbonitrile, (1R*,2R*)- and (1R*,2S*)-2-(4-fluorophenyl)-1,2,3,4-tetrahydro-1-(1H-imidazolylmethyl)naphthalene-6-carbonitrile, (1R*,2R*)- and (1R*,2S)-2-(4-cyanophenyl)-1,2,3,4-tetrahydro-1-(1H-1,2,4-triazol-1-ylmethyl)naphthalene-6-carbonitrile, (1R*,2R*)- and (1R*,2S*)-2-(4-cyanophenyl)-1,2,3,4-tetrahydro-1-(1H-imidazol-1-ylmethyl)naphthalene-6-carbonitrile, and (1R*,2S*)-2-(4-fluorophenyl)-1,2,3,4-tetrahydro-1-(5-methyl-1H-imidazolylmethyl)naphthalene-6-carbonitrile.

The compounds of the formula I may be manufactured by processes known generally for the manufacture of similar compounds. Thus according to a further feature of the invention there is provided a process for the manufacture of a compound of the formula I which comprises the reaction of a compound of the formula II, wherein n, A, $R^1$, $R^2$ and $R^3$ have the meanings stated above, and $R^5$ is a known displaceable radical, with a reactive derivative of a heterocyclic compound of the formula $R^4H$, whereafter
  (i) a compound wherein $R^1$ or $R^2$ is an alkoxy radical is dealkylated to a corresponding compound wherein $R^1$ or $R^2$ is a hydroxy radical;
  (ii) a compound wherein $R^1$ or $R^2$ is an amino, carbamoyl or sulphamoyl radical is alkylated to a corresponding alkylamino, dialkylamino, alkylcarbamoyl, dialkylcarbamoyl, alkylsulphamoyl or dialkylsulphamoyl radical;
  (iii) a compound wherein $R^1$ or $R^2$ is a carbamoyl or cyano radical is hydrolysed and esterified to a corresponding compound wherein $R^1$ or $R^2$ is an alkoxycarbonyl radical;
  (iv) a compound wherein either or both of $R^1$ and $R^2$ is a bromine atom is reacted with cuprous cyanide in an aprotic solvent, for example dimethylformamide, to form a corresponding compound of the invention wherein $R^1$ and/or $R^2$ is a cyano radical.

A suitable value for the displaceable radical $R^5$ is, for example, a halogen atom such as a bromine atom, or a sulphonyloxy radical, such as a mesyl or tosyl radical.

A suitable reactive derivative of a heterocyclic compound of the formula $R^4H$, used as a starting material in the above process, may be, for example, an alkali metal derivative such as the sodium derivative, when $R^4$ is a 1H-1,2,4-triazole or 1H-imidazolyl radical which is linked to A through a nitrogen atom, or a halogen derivative, when $R^4$ is a pyridyl or pyrimidinyl radical which is linked to A through a carbon atom.

Alternatively, a suitable reactive derivative of a heterocyclic compound of the formula $R^4H$ is a 1-trityl-4-alkylimidazole, for example 1-trityl-4-methylimidazole. In this case, the product from the reaction of 1-trityl-4-alkylimidazole with a compound of the formula II is a quaternised compound, which may be converted to the required product, for example by reduction, to remove the protecting trityl group.

The process of the invention is preferably carried out in a suitable solvent, for example acetonitrile, dimethylformamide or N-methylpyrrolidone at room temperature, or at an elevated temperature, up to the boiling point of the solvent.

The starting material of the formula II used in the above process, wherein A is a methylene radical, n is 1, and the side-chain $AR^5$ and the phenyl ring bearing the substituent $R^2$ are in the trans or 1R*,2S* configuration, may be obtained by treating a benzocyclobutane carbonitrile III with a styrene compound IV to form a cyanotetralin derivative V. The cyano group is then reduced in two stages, first to the aldehyde VI with di-isobutylaluminium hydride, and then with lithium aluminium hydride to the alcohol VII. The alcohol VII is then reacted with a phosphorus oxybromide or a sulphonyl chloride to form the required starting material of the formula II. General methods for obtaining the appropriately-substituted benzocyclobutane carbonitriles III are known.

It will be appreciated that, if $R^1$ or $R^2$ is a hydroxy radical, it will be necessary to prepare the corresponding starting material in which such a hydroxy group is protected with a conventional protecting group, which is subsequently removed.

The starting material of the formula II, used in the above process, in which A is a methylene radical, n is 1, $R^3$ is hydrogen and the side-chain $AR^4$ and the phenyl ring bearing the substituent $R^2$ are in the cis or 1R*,2R* configuration, may be obtained from a tetralone VIII which is reacted with trimethylsilylcarbonitrile in the presence of boron trifluoride in dichloromethane to form the corresponding unsaturated nitrile IX, which is then reduced successively with diisobutyl-aluminium hydride to the aldehyde X, and then with lithium aluminium hydride to the alcohol XI. The alcohol XI is then hydrogenated over a palladium catalyst, and the resulting alcohol XII is reacted with phosphorus oxybromide or a sulphonyl chloride to form the required starting material of the formula II in which A is methylene. General methods for obtaining the appropriately-substituted tetralones VIII are known.

Corresponding starting materials wherein A is an alkylene radical such that $R^4$ is separated from the bicyclic ring by a 2-carbon chain may be obtained by reacting a tetralone derivative VIII with an ethyl alpha-bromoalkanoate in the presence of zinc metal in benzene to form the beta-hydroxy ester XIII, which on hydrogenation yields the corresponding ester XIV. Reduction of the ester XIV with lithium aluminium hydride forms the corresponding alcohol XV which is reacted with phosphorus oxybromide or a sulphonyl chloride to produce the required starting material II.

Corresponding starting materials of the formula II wherein A is an alkylene radical of 3 or 4 carbon atoms may be obtained from the tetralone VIII by reaction thereof with an acetylenic silyl ether of the formula HC:C.$(CR_2)_q$OSi$(R^6)_3$, wherein q is 1 or 2, R is hydrogen or an alkyl radical and $R^6$ is an alkyl radical, to form a compound XVI which is hydrogenated to give the corresponding alcohol XVII which in turn is reacted with phosphorus oxybromide or a sulphonyl chloride acid to produce the required starting material II.

Similar starting materials of the formula II wherein $R^3$ is other than hydrogen may be obtained by reaction of a tetralone VIII with butyl-lithium and an alkyl iodide $R^3$I, and then using the 2-alkyltetralone so obtained in place of the tetralone VIII in the above-described reaction sequences.

Starting materials of the formula II in which X is methylene and n is 0 may be obtained by reacting an appropriately-substituted benzyl chloride XVIII with an appropriately-substituted phenylacetic acid XIX to form an indanone derivative XX, which is then used in place of the tetralone VIII in the process described above.

Similar starting materials for compounds of the formula I in which $R^3$ is other than hydrogen may be obtained by alkylating the phenylacetic acid derivative XIX prior to reacting it with the benzyl chloride derivative XVIII.

As indicated above, the compounds of the invention are useful as aromatase inhibitors. Aromatase inhibition may be demostrated by the following tests:

DEMONSTRATION OF ACTIVITY IN VITRO

Aromatase inhibitory activity was measured using the enzyme present in the microsomal fraction of human term placenta, as described by Ryan, J. Biol, Chem. 234, 268, 1959. Enzyme activity was determined by measuring the amount of tritiated water released from 0.5 micromolar (1B,2B-$^3$H)-testosterone after 20 minutes incubation at 37°. The method used was essentially that described by Thomson and Siiteri, J. Biol. Chem. 249, 5364, 1974 except that testosterone was used in place of androstenedione. Test compounds were dissolved in dimethylsulphoxide (DMSO) to achieve final concentrations of 2, 0.2 or 0.02 μg/ml. The reaction was started by the addition of 50 μl of microsome suspension to 50 μl of a solution containing substrate (testosterone) and cofactors (NADPH glucose-6-phosphate and glucose-6-phosphate dehydrogenase) and either DMSO alone or a DMSO solution of test compound. Each concentration of test compound was tested in triplicate. The reaction was stopped by the addition of 200 μl of a 5% (w/v) suspension of charcoal in 0.5% (w/v) solution of Dextran T70 in water. After 1 hour the charcoal was precipitated by centrifugation and 150 μl of supernatant removed and the amount of tritiated water present determined using a liquid scintillation counter. The number of counts in supernatant from incubations containing test compound expressed as a percentage of the counts in supernatant from incubations containing only DMSO was taken as the degree of enzyme inhibition achieved by the test compound.

DEMONSTRATION OF ACTIVITY IN VIVO

Activity in vivo was demonstrated in terms of ovulation inhibition in female rats. Daily vaginal smears were taken from rats housed under controlled lighting (lights on 06.00 hr to 20.00 hr) and those having a vaginal smear pattern consistent with 4-day ovarian cycles were selected. To these rats a single dose of test compound was given either at 16.00 hr on Day 2 of the cycle or at 12.00 hr on Day 3 of the cycle. The rats were then killed in the morning following Day 4 of the cycle—approximately 64 hours after Day 2 treatments or approximately 46 hours after Day 3 treatments—and the presence or absence of eggs in the fallopian tubes determined. The presence of eggs indicates that the rats have ovulated.

Without treatment more than 95% of rats with 4-day ovarian cycles are found to have ovulated at the time of the post-mortem examination. At an effective dose, aromatase inhibitors prevent ovulation ie. no eggs are found in the fallopian tubes.

In the above tests, the compounds of the formula I are active at less than 0.1 μg/ml (in vitro) and less than 10 mg/kg (in vivo), and the preferred compounds of the formula I are active at below 0.01 μg/ml (in vitro) and 1.0 mg/kg (in vivo).

Thus, according to a further feature of the invention there is provided a pharmaceutical or veterinary composition which comprises an effective amount of a compound of the formula I together with a pharmaceutically or veterinarily acceptable diluent or carrier.

The composition of the invention may be in a conventional pharmaceutical form suitable for oral administration, for example a tablet, a capsule, an emulsion or an aqueous or oily solution or suspension. The composition may contain conventional pharmaceutical excipients, and may be manufactured by conventional pharmaceutical techniques.

Preferred pharmaceutical or veterinary compositions of the invention are tablets and capsules containing from 1 to 100, preferably 5 to 50 mg. of a compound of the invention.

The invention is illustrated but not limited by the following Examples. Temperatures are given in degrees Celsius. In reporting NMR data, s=singlet, d=doublet, dd=two doublets, t=triplet, q=quartet, m=multiplet.

EXAMPLE 1

A mixture of methyl (1R*,2R*)-1,2,3,4-tetrahydro-6-methoxy-2-(4-methoxyphenyl)-1-naphthylmethanesulphonate (1 g), imidazole (1.2 g) and potassium carbonate (1.2 g) in acetonitrile (75 ml) was stirred and heated under reflux for 24 h. The acetonitrile was evaporated under reduced pressure, and the residue was dissolved in a mixture of ethyl acetate (50 ml) and water (50 ml). The organic layer was separated, and the aqueous layer was extracted twice with ethyl acetate (50 ml). The combined ethyl acetate extracts were dried and evaporated to dryness, and the residue was purified by flash column chromatography on silica (K60), using ethyl acetate: toluene (1:4 by volume), then ethyl acetate as the eluting solvent, to give (1R*,2R*)-1,2,3,4-tetrahydro-1-(1H-imidazol-1-ylmethyl)-6-methoxy-2-(4- methoxyphenyl)naphthalene as a colourless gum, which crystallised on standing, m.p. 114°.

The methanesulphonate used as starting material in the above process may be obtained as follows:

A mixture of 6-methoxy-2-(4-methoxyphenyl)tetralone (10 g), trimethylsilylcarbonitrile (5.3 g) and boron trifluoride etherate (20 ml of a 45% solution in diethyl ether) in dichloromethane (300 ml) was stirred and heated under reflux in an argon atmosphere for 16 h. The reaction mixture was cooled and then poured onto a mixture of ice and water (300 ml). The organic layer was separated and the aqueous layer extracted twice with dichloromethane (150 ml). The organic extracts were combined, dried and evaporated to dryness. The residual gum was subjected to flash column chromatography on silica (K60) using ethyl acetate:toluene (1:19 by volume) as eluting solvent, to give 3,4-dihydro-6-methoxy-2-(4-methoxyphenyl)naphthalene-1-carbonitrile as a white solid, m.p. 151°.

A solution of the carbonitrile (13.8 g) in toluene (200 ml) was stirred under an argon atomosphere and cooled in an acetone/solid carbon dioxide bath while a solution of di-isobutylaluminium hydride in toluene (25% by weight, 35 ml) was added dropwise over 15 minutes. The reaction mixture was stirred for a further 3 h at room temperature, and was then cooled in an ice/salt bath, and methanol (20 ml) was added dropwise over 10 minutes. This mixture was then poured into a mixture of 3N hydrochloric acid (150 ml) and ice (50 ml), and the resulting mixture stirred for 5 minutes. It was then heated on a steam-bath for 15 minutes and cooled, the toluene layer was separated, and the aqueous layer was extracted twice with ethyl acetate (150 ml). The organic extracts were combined, dried and evaporated to dryness. The residual gum was purified by flash column chromatography on silica (K60) using ethyl acetate:toluene (1:19 by volume) as eluting solvent, to give 3,4-dihydro-6-methoxy-2-(4-methoxyphenyl)naphthalene-1-carbaldehyde as a light yellow solid m.p. 142°.

A solution of this carbaldehyde (11.7 g) in diethyl ether (300 ml) was stirred while a solution of lithium aluminium hydride (1M, 40 ml) was added dropwise over 15 minutes. The reaction mixture was stirred for a further hour at room temperature and then cooled in an ice-bath. Water (1.5 ml) was added dropwise over 20 minutes followed by 10% sodium hydroxide solution (15 ml) and finally water again (4.5 ml). Stirring was continued for 30 minutes until the solid precipitate was of a uniform nature. The solid was filtered off and washed with diethyl ether (200 ml). The filtrate and ethereal washings were combined and evaporated to dryness, and the residual gum was triturated with diethyl ether to give 3,4-dihydro-6-methoxy-2-(4-methoxyphenyl)naphthalene-1-methanol as a solid m.p. 121°.

A mixture of this naphthalene-1-methanol compound (10.3 g) and 10% palladium on charcoal (2 g) in ethyl acetate (200 ml) was stirred rapidly under an atmosphere of hydrogen for 1 hour. The catalyst was removed by filtration, and the filtrate was evaporated to dryness. The residual gum was purified by flash column chromatography on silica (K60), using ethyl acetate:toluene (1:9 by volume), then ethyl acetate:toluene (1:4 by volume), as eluting solvents to give 1,2,3,4-tetrahydro-6-methoxy-2-(4-methoxyphenyl)naphthalene-1-methanol as a solid, m.p. 84°.

A mixture of the tetrahydronaphthalene-1-methanol compound (9.4 g) and triethylamine (9.6 g) in dichloromethane (200 ml) was stirred and cooled in an ice-bath under an argon atmosphere while a solution of methanesulphonyl chloride (7.2 g) in dichloromethane (30 ml) was added dropwise over 15 minutes. The reaction mixture was then stirred at 20° for 1 hour, and poured into a mixture of 2N hydrochloric acid (200 ml) and ice (200 ml). The organic layer was separated, and the aqueous layer extracted twice with dichloromethane (100 ml). The organic extracts were combined, dried, and evaporated to dryness. The residual oil was subjected to flash column chromatography on silica (K60), using ethyl acetate:toluene (1:4 by volume) as eluting solvent, to give the required methanesulphonate starting material as a colourless gum which solidified on standing, m.p. 108°.

EXAMPLES 2–6

The process described in Example 1 was repeated, using the appropriately substituted 1-naphthylmethanesulphonate, and 1H-1,2,4-triazole or 1H-imidazole as appropriate, as starting materials, to give the following compounds:

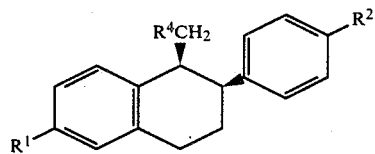

| Ex. | $R^1$ | $R^2$ | $R^4$ | M.p. | Footnotes |
|---|---|---|---|---|---|
| 2 | MeO | MeO | T* | 101 | 1,2,3,4 |
| 3 | MeO | F | T | | 5 |
| 4 | MeO | F | I* | | 6 |
| 5 | F | F | T | 129 | 7,8,9,10 |
| 6 | F | F | I | 112 | 7,8,9,10 |

*T = 1H-1,2,4-triazol-1-yl; I = 1H-imidazol-1-yl.
Footnotes
1. 3,4-Dihydronaphthalene-1-carbaldehyde precursor, m.p. 142°.
2. 3,4-Dihydronaphthalene-1-methanol precursor, m.p. 121°.
3. 1,2,3,4-Tetrahydronaphthalene-1-methanol precursor, m.p. 84°.
4. Methanesulphonate precursor, m.p. 108°.
5. Nmr in CDCl$_3$: δ7.9(1H,s), 7.3(3H,m), 7.1(2H,m), 6.7(1H,d), 6.55(1H,2xd), 6.15(1H,d), 4.0(2H,m), 3.75(3H,s), 3.6(1H,m), 3.45(1H,m), 3.0(2H,m), 2.1(2H,m).
6. Nmr in CDCl$_3$: δ7.3(3H,m), 7.1(2H,m), 6.95(2H,d), 6.7(1H,d), 6.6(1H,2xd), 6.45(1H,s), 6.3(1H,d), 3.8(5H,m), 3.3(2H,m), 3.0(2H,m), 2.0(2H,m).
7. The 3,4-dihydronaphthalene-1-carbaldehyde precursor was obtained as follows: A mixture of 6-fluoro-2-(4-fluorophenyl)tetralone (18.4 g), trimethylsilylcarbonitrile (10.72 ml) and 18-crown-6/potassium cyanide complex (100 mg) in benzene (50 ml) was stirred under an argon atmosphere at room temperature for 1½h. The reaction mixture was evaporated to dryness and the residual oil was purified by flash column chromatography on silica (K60) using ethyl acetate:hexane (1:9 by volume) to give 6-fluoro-2-(4-fluorophenyl)-1-(trimethylsilyloxy)-naphthalene-1-carbonitrile as a solid m.p. 68°.
A mixture of this carbonitrile (17 g) and phosphoryl chloride (17 ml) in pyridine (100 ml) was stirred and heated at reflux under an argon atmosphere for 16h. The reaction mixture was cooled and poured into a mixture of 2N hydrochloric acid (800 ml) and ice (200 ml). It was then extracted three times with ethyl acetate (600 ml), and the extracts were combined, dried, and evaporated to dryness. The residual gum was subjected to flash column chromatography on silica (K60), using toluene as eluting solvent, to give 6-fluoro-2-(4-fluorophenyl)-3,4-dihydronaphthalene-1-carbonitrile, as a white solid, m.p. 146°.
8. 3,4-Dihydronaphthalene-1-carbaldehyde precursor, m.p. 144°.
9. 3,4-Dihydronaphthalene-1-methanol precursor, m.p. 104°.
10. 1,2,3,4-Tetrahydronaphthalene-1-methanol precursor, m.p. 127°.

EXAMPLE 7

The process described in Example 1 was repeated, using the corresponding 1-naphthylethanesulphonate as starting material, to give (1R*,2R*)-1,2,3,4-tetrahydro-1-[2-(1H-imidazol-1-yl)ethyl]-6-methoxy-2-(4-methoxyphenyl)naphthalene, m.p. 121°.

The 2-[1,2,3,4-tetrahydro-6-methoxy-2-(4-methoxyphenyl)-1-naphthyl]ethanesulphonate used as starting material in the above process was obtained as follows:

6-Methoxy-2-(4-methoxyphenyl)tetralone (15 g) and ethyl bromoacetate (26.6 g) were dissolved in benzene (250 ml), zinc dust (17.4 g) and a crystal of iodine were added, and the mixture was stirred and heated under reflux in an atmosphere of argon for 30 minutes. The reaction mixture was cooled and added to a saturated solution of ammonium chloride (250 ml). The organic layer was separated and the aqueous phase was extracted with ethyl acetate (200 ml). The organic extracts were combined, dried, and evaporated to dryness to give ethyl 2-[1,2,3,4-tetrahydro-6-methoxy-2-(4-methoxyphenyl)-1-naphthyl]-2-hydroxyacetate as a gum.

The hydroxyacetate (19 g) was dissolved in ethyl acetate (500 ml), 10% palladium on charcoal (3 g) was added, and the mixture was stirred rapidly under an atmosphere of hydrogen for 24 hours. The catalyst was removed by filtration and the filtrate evaporated to dryness. The residual oil was purified by flash column chromatography on silica (K60) using ethyl acetate:toluene (1:10 by volume) as eluting solvent, to give ethyl 1,2,3,4-tetrahydro-6-methoxy-2-(4-methoxyphenyl)-1-naphthylacetate as a white solid, m.p. 81° C.

A suspension of lithium aluminium hydride (4.62 g) in diethyl ether (300 ml) was stirred and cooled in an ice-bath while a solution of the 1-naphthylacetate (8.6 g) in diethyl ether (200 ml) was added dropwise over 30 minutes. The reaction mixture was stirred for 1 h at 0°, then water (4.6 ml) was added dropwise to the reaction mixture, followed by a solution of 1N sodium hydroxide (4.6 ml) and finally more water (15 ml). The solid precipitate was filtered off and washed with diethyl ether (200 ml). The washings and filtrate were combined and evaporated to dryness, to give 2-[1,2,3,4-tetrahydro-6-methoxy-2-(4-methoxyphenyl)-1-naphthyl]ethanol as an oil which solidified on trituration with petroleum ether (b.p. 60°-80°) to give a solid, m.p. 95°.

This 1-naphthylethanol was then reacted with methanesulphonyl chloride, as described for the corresponding 1-naphthylmethanol in the last part of Example 1, to give the required substituted methyl 1-naphthylethanesulphonate starting material, m.p. 126°.

EXAMPLE 8

The process described in Example 7 was repeated, using 1H-1,2,4-triazole in place of imidazole, to give (1R*,2R*)-1,2,3,4-tetrahydro-6-methoxy-2-(4-methoxyphenyl)-1-[2-(1H-1,2,4-triazol-1-yl)ethyl]naphthalene, as gum. NMR in CDCl$_3$: δ7.85(1H, s), 7.7(1H, s), 7.15(2H, m), 6.9(3H, m), 6.7(2H, m), 3.8(8H, m), 3.2(1H, 2xt), 2.9(3H, m), 2.0(4H, m).

EXAMPLE 9

The process described in Example 1 was repeated, using the corresponding 3-(1-naphthyl)propanesulphonate, m.p. 67°, as starting material, to give 1R*,2R*)-1,2,3,4-tetrahydro-6-methoxy-2-(4-methoxyphenyl)-1-[3-(1H-imidazol-1-yl)propyl]-naphthalene, m.p. 133°.

The propanesulphonate starting material used in the above process was obtained as follows:

A solution of prop-1-yn-3-ol tetrahydropyranyl ether (15 g) in tetrahydrofuran (200 ml) was stirred under an argon atmosphere while a solution of methylmagnesium chloride (27.3 mls, 2.6 m in tetrahydrofuran) was added over 10 minutes. The mixture was warmed to reflux and heated for 45 mins. A solution of 1,2,3,4-tetrahydro-6-methoxy-2-(4-methoxyphenyl)tetralone (10 g) in tetrahydrofuran (100 ml) was then added and the heating continued for another 45 mins. The mixture was then cooled in an ice-bath, and saturated ammonium chloride solution (300 mls) was added. The tetrahydrofuran layer was separated and the aqueous layer was further extracted with ethyl acetate (2×100 ml). The organic extracts were combined, dried and evaporated to half the volume. To this solution was added 10% palladium on charcoal (3 g) and the resulting mixture was stirred under a hydrogen atmosphere for 16 h. The catalyst was filtered off, and the filtrate was evaporated to dryness to give 1,2,3,4-tetrahydro-6-methoxy-2-(4-methoxyphenyl)-1-[3-(tetrahydropyranyloxy)propyl]-naphthalene as a colourless gum.

A mixture of this gum, dissolved in ethanol (150 ml) and 3N hydrochloric acid (35 ml) was heated on a steam-bath for 2½ h. The ethanol was evaporated, and the residue was basified with saturated sodium bicarbonate solution. It was then extracted 3 times with ether (300 ml), and the extracts were combined, dried, and evaporated to dryness. The residual gum was purified by flash column chromatography on solica (K60), using ethyl acetate:toluene (1:9 by volume) as eluting solvent, to give 3-[(1R*,2R*)-1,2,3,4-tetrahydro-6-methoxy-2-(4-methoxyphenyl)-1-naphthyl]propanol, m.p. 99°. This propanol derivative was then reacted with methanesulphonyl chloride, as described for the corresponding methanesulphonate starting material in the last part of Example 1, to give the required propanesulphonate starting material.

EXAMPLE 10

The process described in Example 9 was repeated, using 1H-1,2,4-triazole in place of 1H-imidazole, to give (1R*,2R*)-1,2,3,4-tetrahydro-6-methoxy-2-(4-methoxyphenyl)-1-[3-(1H-1,2,4-triazol-1-ylpropyl)]naphthalene, m.p. 90°.

EXAMPLE 11

The process described in Example 1 was repeated, using the corresponding (1R*,2S*)-methanesulphonate starting material, to give (1R*,2S*)-1,2,3,4-tetrahydro-1-(1H-imidazol-1-ylmethyl)-6-methoxy-2-(4-methoxyphenyl)naphthalene, m.p. 132°.

The (1R*,2S)-methanesulphonate used as starting material in the above process was obtained as follows:

A mixture of 4-methoxybenzocyclobutane-1-carbonitrile (16 g) and 4-methoxystyrene (23.5 g) was stirred and heated at 175° for 45 minutes. The mixture was cooled, and purified by flash column chromatography on silica (K60), eluting with a mixture of ethyl acetate and petroleum ether (b.p. 40°-60°), 1:9 by volume, to give 1,2,3,4-tetrahydro-6-methoxy-2-(4-methoxyphenyl)naphthalene-1-carbonitrile, m.p. 127°.

This material was then used in place of 3,4-dihydro-6-methoxy-2-(4-methoxyphenyl)naphthalene-1-carbonitrile in the reaction sequence described in the latter part of Example 1, but omitting the hydrogenation step, to give successively the corresponding carbaldehyde, m.p. 110°, the corresponding (1R*,2S*)-methanol derivative, m.p. 92°, and the required methanesulphonate starting material, m.p. 84°.

EXAMPLES 12-16

The process described in Example 11 was repeated, using the appropriately-substituted 1-naphthylmethanesulphonate, and 1H-1,2,4-triazole or 1H-imidazole as appropriate, to give the following compounds:

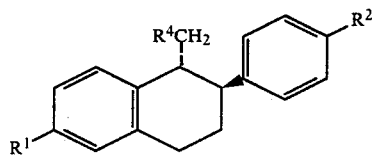

| Ex. | R¹ | R² | R⁴ | M.p. | Footnotes |
|---|---|---|---|---|---|
| 12 | MeO | MeO | T* | 115 | |
| 13 | MeO | F | I* | 116 | 1,2 |
| 14 | MeO | F | T | 97 | 1,2 |
| 15 | MeO | Cl | I | 145 | 3 |
| 16 | MeO | Cl | T | | 3,4 |

*T = 1H-1,2,4-triazol-1-yl; I = 1H-imidazol-1-yl.
Footnotes
1. Carbonitrile precursor, m.p. 107°
2. Carbaldehyde precursor, m.p. 105°
3. Carbonitrile precursor, m.p. 145°
4. Nmr in CDCl₃: δ7.9(1H,s), 7.6(1H,s), 7.25(3H,m), 7.15(2H,m), 6.95(1H,d), 6.75(1H,2xd), 6.6(1H,d), 4.4(2H,m), 3.8(3H,s), 3.55(1H,m), 2.9(1H,m), 1.9(2H,m).

EXAMPLE 17

A solution of (1R*,2R*)-1,2,3,4-tetrahydro-1-(1H-imidazol-1-ylmethyl)-6-methoxy-2-(4-methoxyphenyl)-naphthalene, (prepared as described in Example 1), in dichloromethane (20 ml) was stirred in an argon atmosphere and cooled in an acetone/solid carbon dioxide bath while a 1M solution of boron tribromide was added dropwise over 5 minutes. The mixture was kept at −20° for 48 h, then poured into a mixture of saturated sodium bicaronate solution (30 ml) and stirred vigorously for 2 h. The solid thus obtained was filtered off, washed with water (100 ml) then dichloromethane (100 ml) and dried in a desiccator under reduced pressure to give (1R*,2R*)-1,2,3,4-tetrahydro-6-hydroxy-2-(4-hydroxyphenyl)-1-(1H-imidazol-1-ylmethyl)naphthalene, m.p. 238°.

EXAMPLES 18–27

The process described in Example 17 was repeated, using the appropriate methoxy-substituted compounds as starting materials, to give the following compounds:

| Ex | R¹ | R² | n | R⁵ | stereo. chemistry | M.p. |
|---|---|---|---|---|---|---|
| 18 | OH | OH | 1 | T (a) | 1R*,2R* | 151 |
| 19 | OH | OH | 2 | I (a) | 1R*,2R* | 242 |
| 20 | OH | OH | 2 | T | 1R*,2R* | 196 |
| 21 | OH | OH | 3 | I | 1R*,2R* | 206 |
| 22 | OH | OH | 3 | T | 1R*,2R* | 211 |
| 23 | OH | OH | 1 | I | 1R*,2S* | 248 |
| 24 | OH | OH | 1 | T | 1R*,2S* | 250 |
| 25 | OH | F | 1 | I | 1R*,2S* | 146 |
| 26 | OH | F | 1 | T | 1R*,2S* | 168 |
| 27 | OH | Cl | 1 | T | 1R*,2S* | 178 |

(a) T = 1H-1,2,4-triazol-1-yl; I = 1H-imidazol-1-yl.

EXAMPLE 28

The process described in Example 1 was repeated, using the appropriately-substituted 2-methyl-1-naphthylmethylsulphonate as starting material, to give (1R*,2R*)-1,2,3,4-tetrahydro-6-methoxy-2-(4-methoxyphenyl)-2-methyl-1-(1H-1,2,4-triazol-1-ylmethyl)naphthalene, as a gum. Nmr in CDCl₃, δ7.95(1H, s), 7.45(2H, d), 7.25(1H, s), 6.95(2H, d), 6.7(1H, d), 6.55(1H, dd), 6.05(1H, d), 3.9(1H, dd), 3.85(3H, s), 3.75(3H, s), 3.65(1H, dd), 3.5(1H, m), 3.05(2H, m), 2.2(1H, m), 2.1(1H, m), 1.25(3H, s).

The 2-methyl-1-naphthylmethylsulphonate used as the starting material in the above process may be obtained as follows:

A suspension of (methoxymethyl)triphenylphosphonium chloride (25.7 g) in diethyl ether (400 ml) was stirred under an argon atmosphere and cooled in an ice-bath while a solution of n-butyl-lithium in hexane (1.6M, 46 ml) was added slowly over 10 minutes. The reaction mixture was then stirred at that temperature for 1 hour. A solution of 6-methoxy-2-(4-methoxyphenyl)-2-methyltetralone (8.9 g ) in diethyl ether 150 ml) was added to the reaction, and it was then stirred at room temperature for 16 h, saturated ammonium chloride solution (300 ml) was added to the reaction mixture and the organic layer was separated. The aqueous layer was extracted twice with diethyl ether (200 ml). The organic extracts were combined, dried and evaporated to dryness. The resulting gum was subjected to flash column chromatography on silica (K60) using toluene as eluting solvent to give 6-methoxy-1-methoxymethylene-2-(4-methoxyphenyl)-2-methylnaphthalene as a colourless oil.

A solution of this material (3 g) and perchloric acid (2 ml) in diethyl ether (100 ml) was stirred at room temperature for 16 h, then water (50 ml) was added. The organic layer was separated and the aqueous layer was washed twice with diethyl ether (100 ml). The combined ether extracts were dried, and evaporated to dryness. The residual oil was subjected to flash column chromatography on silica (K60), eluting with ethyl acetate:toluene (1:19 by volume) to give a colourless gum which crystallised on trituration with diethyl ether to give a white solid. Recrystallisation of this material from ethyl acetate:hexane (b.p. 67°–70°) gave (1R*,2R*)-6-methoxy-2-(4-methoxyphenyl)-2-methylnaphthalene-1-carbaldehyde, m.p. 127°.

The mother liquors were evaporated to dryness, and rechromatographed under the same conditions to give the corresponding (1R*,2S*) isomer as a gum, which is the required precursor for Example 29.

The (1R*,2R*)-carbaldehyde was then used in place of the carbaldehyde used in the process described in the latter part of Example 1 to give successively the corresponding methanol derivative, m.p. 149°, and the required 1-naphthylmethanesulphonate starting material as a gum.

EXAMPLE 29

The process described in Example 28 was repeated, using the corresponding (1R*,2S*)-2-methyl-1-naphthylmethane-sulphonate as starting material, to give (1R*,2S*)-1,2,3,4-tetrahydro-6-methoxy-2-(4-methoxyphenyl)-2-methyl-1-(1H-1,2,4-triazol-1-ylmethyl)naphthalene as a gum. Nmr in CDCl₃: δ7.9(1H, s), 7.55(1H, s), 7.1(2H, d), 7.0(1H, d), 6.8(3H, m), 4.6(2H, m), 3.8(6H, d), 3.55(1H, q), 2.6(2H, t), 1.9(2H, m), 1.35(3H, s).

The starting material required for the above process is obtained as described in the latter part of Example 28, but using the (1R*,2S*)-2-methylnaphthalene-1-carbaldehyde precursor in place of the (1R*,2R*) isomer used in Example 28, to give successively the corresponding methanol derivative and the corresponding 1-naphthylmethanesulphonate, both as gums.

EXAMPLE 30

The process described in Example 1 was repeated using 4-methylimidazole in place of imidazole, and isolating the less polar isomer by chromatography to give (1R*,2R*)-1,2,3,4-tetrahydro-6-methoxy-2-(4-methoxyphenyl)-1-(4-methylimidazol-1-naphthalene, as a gum. Nmr spectrum in CDCl$_3$: δ 7.2(2H, d), 6.95(2H, d); 6.8(1H, d); 6.7(1H, s); 6.6(1H, dd); 6.3(1H, d); 6.2(1H, s); 3.85(3H, s); 3.8(3H, s); 3.65(2H, m); 3.1(4H, m); 2.15(3H, s); 2.0(2H, m).

EXAMPLE 31

A mixture of methyl (1R*,2R*)-1,2,3,4-tetrahydro-6-methoxy-2-(4-methoxyphenyl)-1-naphthylmethanesulphonate (0.2 g) and 1-trityl-4-methylimidazole (0.172 g) in acetonitrile (10 ml) was stirred and heated under reflux for 72 h. The acetonitrile was evaporated under reduced pressure, and the residue was dissolved in 90% by volume aqueous acetic acid (20 ml). This acetic acid solution was heated under reflux for 24 h, and then evaporated to dryness under reduced pressure, and the residue was dissolved in a mixture of ethylacetate (25 ml) and water (25 ml). The organic layer was separated and the aqueous layer was extracted twice with ethyl acetate (40 ml). The combined ethyl acetate solutions were dried and evaporated to dryness, and the residue was purified by flash column chromatography on silica (K60), using methanol/dichloromethane, 2:98 by volume, then methanol/dichloromethane, 5:95 by volume, as the eluting solvent, to give (1R*,2R*)-1,2,3,4-tetrahydro-6-methoxy-2-(4-methoxyphenyl)-1-(5-methylimidazol-1-ylmethyl)naphthalene as a colourless gum. Nmr in CDCl$_3$: δ 7.25(2H, d); 6.95(3H, m); 6.7(2H, m); 6.5(1H, dd); 5.95(1H, d); 3.85(3H, s); 3.8(3H, s); 3.65(2H, m); 3.3(1H, m); 3.05(3H, m); 2.15(2H, m); 1.65 (3H, s).

EXAMPLE 32

The process described in Example 28 was repeated, using methyl (1R*,2S*)-6-fluoro-2-(4-fluorophenyl)-1,2,3,4-tetrahydro-2-methyl-1-naphthylmethanesulphonate as starting material, to give (1R*,2S*)-6-fluoro-2-(4-fluorophenyl)-1,2,3,4-tetrahydro-2-tetrahydro-2-methyl-1-(1H-1,2,4-triazol-1-ylmethyl)naphthalene. Nmr in CDCl$_3$: δ 8.0(1H, s); 7.5(1H, s); 7.25(2H, m); 6.9(2H, m); 6.65(2H, m); 6.25(1H, dd); 4.65(1H, dd); 4.2(1H, dd); 3.85(1H, dd); 2.85(1H, m); 2.6(1H, m); 2.3(1H, m); 1.95(1H, m); 1.45(3H, s).

The methanesulphonate starting material used in the above process was obtained by the sequence of processes described in the latter part of Example 28, starting from 6-fluoro-2-(4-fluorophenyl)-2-methyltetralone in place of the tetralone starting material there described.

EXAMPLES 33–36

The process described in Example 7 was repeated, using the appropriately-substituted 1-naphthylethanesulphonates as starting materials, to give the following compounds:

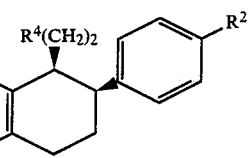

| Ex. | R$^1$ | R$^2$ | R$^4$ | M.p. |
|---|---|---|---|---|
| 33 | F | F | T* | 78–79 |
| 34 | F | F | I* | 109 |
| 35 | F | Cl | T | 82 |
| 36 | F | Cl | I | 104–105 |

*T = 1H-1,2,4-triazol-1-yl, I = 1H-imidazol-1-yl.

The 1-naphthylethylsulphonate starting materials were manufactured by the process described in the latter part of Example 7.

EXAMPLES 37

The process described in Example 1 was repeated, using the appropriate 1,2,3,4-tetrahydro-1-naphthylmethanesulphonate as starting material, to give (1R*,2R*)-2-(4-fluorophenyl)-1,2,3,4-tetrahydro-1-(1H-1,2,4-triazol-1-ylmethyl)naphthalene-6-carbonitrile, m.p. 149°.

The naphthylmethanesulphonate starting material used in the manufacture of Example 37 was obtained by converting 6-bromo-2-(4-fluorophenyl)tetralone to the corresponding nitrile, then to the corresponding aldehyde, and then to the corresponding methanol derivative by the general sequence of processes described in the second part of Example 1.

A mixtuure of 6-bromo-4-(2-fluorophenyl)-3,4-dihydro-1-naphthylmethanol (5 g) and cuprous cyanide (13.45 g) in dimethylformamide (100 ml) was stirred and heated under reflux in an atmosphere of argon for 20 h. The mixture was then cooled, poured into water (400 ml) and extracted with ethyl acetate (300 ml). The ethyl acetate extract was dried and evaporated to dryness, and the residue was purified by flash column chromatography on silica, eluting with ethyl acetate/toluene, 1:9 by volume, to give 6-(2-fluorophenyl)-7,8-dihydro-5-hydroxyethylnaphthalene-2-carbonitrile, m.p. 142°.

This methanol derivative was then converted to the required (1R*,2R*)-1,2,3,4-tetrahydro-1-naphthylmethanesulphonate, m.p. 119°, by the general sequence of reactions described in the latter part of Example 1.

EXAMPLES 38–46

The process described in Example 1 was repeated, using the appropriate 1,2,3,4-tetrahydro-1-naphthylsulphonate as starting material, to give the following compounds:

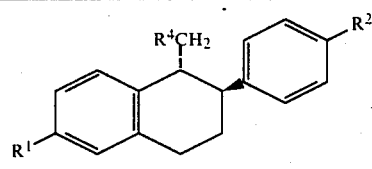

| Ex | R$^1$ | R$^2$ | R$^4$ | M.p. |
|---|---|---|---|---|
| 38 | CN | F | T* | 144 |
| 39 | CN | F | I* | 104 |
| 40 | CN | F | 5-me-I* | 116 |
| 41 | F | CN | T | 121 |
| 42 | F | CN | I | 116 |

-continued

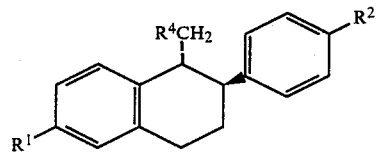

| Ex | R¹ | R² | R⁴ | M.p. |
|---|---|---|---|---|
| 43 | CN | H | J | 135 |
| 44 | CN | H | I | 105 |
| 45 | CN | CN | T | 153 |
| 46 | CN | CN | I | 165 |

*T = 1H-1,2,4-trizaol-1-yl, I = 1H-imidazol-1-yl, 5-Me—I = 5-methyl-1H-imidazol-1-yl.

The naphthylmethanesulphonate starting materials used in the manufacture of Examples 38–40 was obtained from 6-bromo-2-(4-fluorophenyl)-3,4-dihydronaphthalene-1-carbonitrile, obtained by the process described in the second part of Example 37, as follows:

A mixture of 6-bromo-2-(4-fluorophenyl)-3,4-dihydronaphthalene-1-carbonitrile (8 g), magnesium (3 g), tetrahydrofuran (300 ml) and methanol (300 ml) was stirred at 0° under an atmosphere of argon for 1.5 h. The reaction mixture was then poured into 2N hydrochloric acid (300 ml), and the organic solvents were evaporated under reduced pressure. The residue was extracted with ethyl acetate (300 ml), the extract was dried and evaporated to dryness and the residue was triturated with diethyl ether to give 6-bromo-2-(4-fluorophenyl)-1,2,3,4-tetrahydronaphthalene-1-carbonitrile as a white solid, m.p. 146°.

The nitrile was then converted to the corresponding 1,2,3,4-tetrahydro-1-carbaldehyde, by the general process described in the second part of Example 1, and this tetrahydrocarbaldehyde was then used in place of the dihydrocarbaldehyde in the reaction sequence described in the latter part of Example 1 to give the required (1R*,2S*)-1,2,3,4-tetrahydro-1-naphthylmethanesulphonate starting material, m.p. 134°.

The other (1R*,2S*)-1,2,3,4-tetrahydro-1-naphthylmethanesulphonates required as starting materials for Examples 41–46 were obtained similarly, from the appropriately substituted 3,4-dihydronaphthalene-1-carbonitriles, obtained as described in the latter part of Example 37.

| Starting materials for Examples | Intermediate | M.p. |
|---|---|---|
| 41, 42 | dihydrocarbonitrile | 121 |
|  | tetrahydrocarbonitrile | 108 |
|  | methanesulphonate | (a) |
| 43, 44 | methanesulphonate | 120 |
| 45, 46 | dihydrocarbonitrile | 156 |
|  | tetrahydrocarbonitrile | 111 |
|  | methanesulphonate | 193 |

(a) NMR in CDCl₃: δ 7.6(2H,d); 7.25(3H,m); 6.9(2H,m); 4.4(1H,q); 4.3(1H,q); 3.35(2H,m); 2.85(3H,s); 2.7(2H,m); 2.05(2H,m).

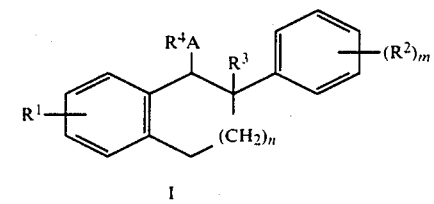

I

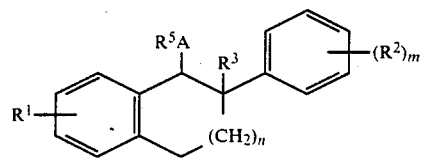

II

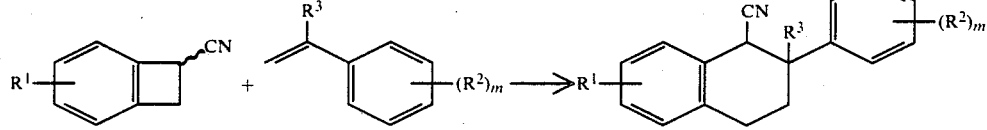

III  IV  V

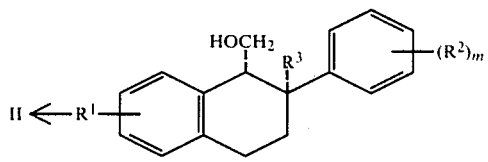

VII

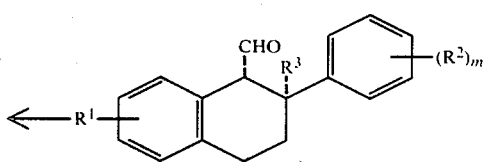

VI

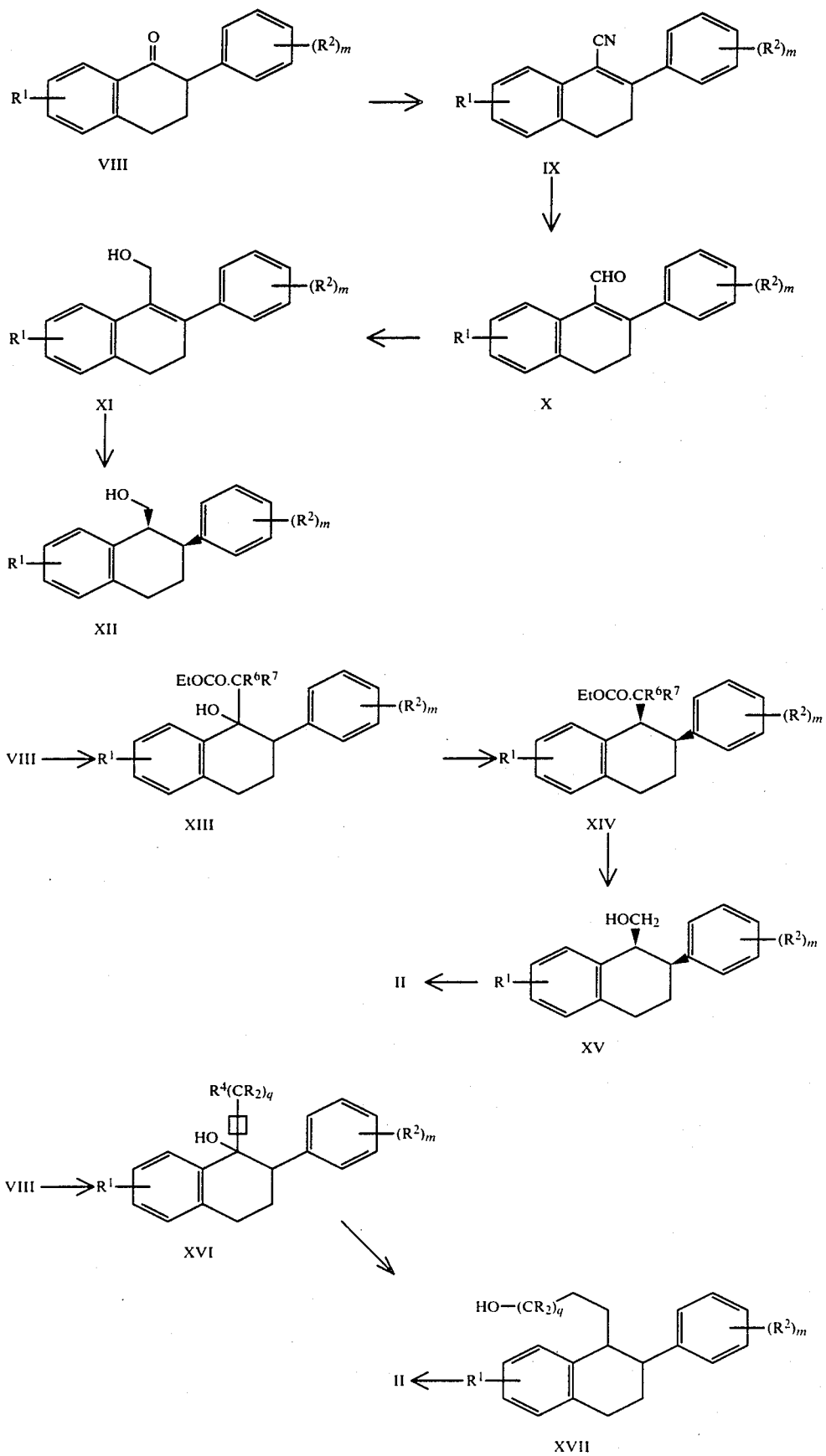

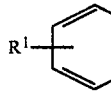 + 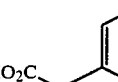 → 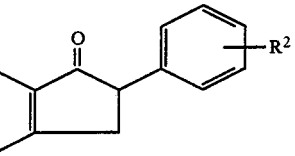

XVIII  XIX  XX

We claim:

1. A heterocyclic compound of the formula I:

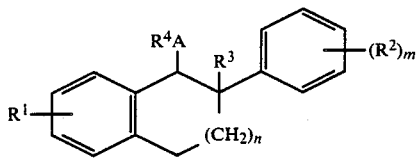

in which n is 0 or 1; A is a 1-4C alkylene radical which may optionally bear one or more 1-4C alkyl substituents; $R^1$ and $R^2$, which may be the same or different, are each a hydrogen or halogen atom, an amino, carbamoyl, cyano, hydroxy, nitro or sulphamoyl radical, a 1-6C alkyl, 1-6C halogenalkyl, 1-6C alkoxy, 1-6C halogenoalkoxy, 1-6C alkylamino, (1-6C alkyl)carbamoyl or 1-6C alkylsulphamoyl radical, a di(1-6C alkyl)-amino, di(1-6C alkyl)carbamoyl or di(1-6C alkyl)sulphamoyl radical, or a 2-7C alkoxycarbonyl radical; m is an integer of 1 to 5, $R^3$ is a hydrogen or halogen atom or a 1-6C alkyl or 1-6C halogenoalkyl radical; and $R^4$ is a 1,2,4-triazole or imidazole ring which may bear a 1-6C alkyl substituent; and for those compounds which contain a basic nitrogen atom, the pharmaceutically acceptable acid addition salts thereof.

2. A heterocyclic compound as claimed in claim 1 in which A is an ethylidene, propylidene, butylidene, pentylidene, 1-methylethylidene, 1-methylbutylidene, 1-ethylethylidine, 1- or 2-methylethylene, 1- or 2-ethylethylene, 1,2-dimethylethylene, 1-, 2- or 3-methyltrimethylene, 1,2-, 1,2- or 2,3-dimethyltrimethylene, 1-, 2-, 3- or 4-methyltetramethylene of 1,2-, 1,3-, 1,4-, 2,3- or 3,4-dimethyltetramethylene radical, $R^1$ and $R^2$ are each a hydrogen, chlorine, fluorine, bromine or iodine atom, an amino, carbamoyl, cyano, hydroxy, nitro, sulphamoyl, methyl, ethyl, propyl, isopropyl, butyl, isobutyl, sec-butyl, tert-butyl, pentyl, hexyl, fluoromethyl, (dichloromethyl,) difluoromethyl, trichloromethyl, trifluoromethyl, 2-chloroethyl, 2-fluoroethyl, 2,2,2-trichloroethyl, 2,2,2-trifluoroethyl, 1,1,2,2-tetrafluoroethyl, 3,3,3-trifluoropropyl, 2,2,3,3-tetrafluoropropyl, perfluoropropyl, 4,4,4-trifluorobutyl, methoxy, ethoxy, propoxy, isopropoxy, butoxy, isobutoxy, sec-butoxy, tert-butoxy, pentyloxy, hexyloxy, a fluoromethoxy, difluoromethoxy, trifluoromethoxy, 2-fluoroethoxy, 2,2-difluoroethoxy, 2,2,2-trifluoroethoxy, 1,1,2-trifluoroethoxy, 2,2,3,3-tetrafluoropropoxy, 1-methyl-2,2,2-trifluoroethoxy, methylamino, ethylamino, propylamino, isopropylamino, butylamino, isobutylamino, pentylamino, hexylamino, dimethylamino, diethylamino, ethylmethylamino, dipropylamino, methylpropylamino, dihexylamino, methylcarbamoyl, ethylcarbamoyl, propylcarbamoyl, isopropylcarbamoyl, hexylcarbamoyl, dimethylcarbamoyl, diethylcarbamoyl, ethylmethylcarbamoyl, dipropylcarbamoyl, methylpropylcarbamoyl, dihexylcarbamoyl, methylsulphamoyl, ethylsulphamoyl, propylsulphamoyl, hexylsulphamoyl, dimethylsulphamoyl, diethylsulphamoyl, ethylmethylsulphamoyl, dipropylsulphamoyl, dihexylsulphamoyl, methyoxycarbonyl, ethoxycarbonyl, propoxycarbonyl, isopropoxycarbonyl or hexyloxycarbonyl radical, $R^3$ is a hydrogen, chlorine, fluorine, bromine or iodine atom, or a methyl, ethyl, propyl, isopropyl, butyl, isobutyl, sec-butyl, tert-butyl, pentyl, hexyl, fluoromethyl, (dichloromethyl,) difluoromethyl, trichloromethyl, trifluoromethyl, 2-chloroethyl, 2-fluoroethyl, 2,2,2-trichloroethyl, 2,2,2-trifluoroethyl, 1,1,2,2-tetrafluoroethyl, 3,3,3-trifluoropropyl, 2,2,3,3-tetrafluoropropyl, perfluoropropyl or 4,4,4-trifluorobutyl radical, and $R^4$ is a 1H-1,2,4-triazolyl, 1H-imidazolyl, pyridyl or pyrimidinyl radical which may bear a methyl, ethyl or hexyl substituent, or a hydrochloride, nitrate, sulphate, acetate or phosphate thereof.

3. A heterocyclic compound as claimed in claim 2 wherein n is 1, A is methylene, ethylene or trimethylene radical, $R^1$ and $R^2$, which may be the same or different, are each a chlorine or fluorine atom, or a carbamoyl, cyano, hydroxy, methoxy, trifluoromethyl or trifluoromethoxy radical, m is 1 or 2, $R^3$ is a hydrogen atom or a methyl radical, and $R^4$ is a 1H-1,2,4-triazol-1-yl, 1H-imidazol-1-yl, 4-methyl-1Himidazol-1-yl, 5-methyl-1H-imidazol-1-yl, 3-pyridyl or 5-pyrimidinyl radical.

4. A heterocyclic compound as claimed in claim 3 wherein n is 1, A is a methylene, ethylene or trimethylene radical, $R^1$ and $R^2$, which may be the same or different, are each a chlorine or fluorine atom, or a cyano, hydroxy or methoxy radical, m is 1 or 2, $R^3$ is a hydrogen atom or a methyl radical, and $R^4$ is a 1H-1,2,4-triazol-1-yl, 1H-imidazol-1-yl, 4-methyl-1H-imidazol-1-yl or 5-methyl-1H-imidazol-1-yl radical.

5. A heterocyclic compound as claimed in claim 4 wherein m is 1 and the substituent $R^2$ is in the 4-position of the phenyl ring.

6. A heterocyclic compound as claimed in claim 4 or 5 wherein n is 1, A is a methylene radical, m is 1 or 2, one of $R^1$ and $R^2$ is a cyano radical, and the other of $R^1$ and $R^2$ is a chlorine or fluorine atom or a cyano radical.

7. A heterocyclic compound as claimed in claim 6 wherein m is 1 and $R^1$ and $R^2$ are selected from fluorine atoms and cyano radicals.

8. A heterocyclic compound as claimed in claim 4 which is (1R*,2R*)-6-fluoro-2-(4-fluorophenyl)-1,2,3,4-tetrahydro-1-(1H-1,2,4-triazol-1-ylmethyl)naphthalene, (1R*,2R*)-6-fluoro-2-(4-fluorophenyl-1,2,3,4-tetrahydro-1-(1H-imidazolylmethyl)naphthalene, (1R*,2R*)- and (1R*,2S*)-2-(4-fluorophenyl)-1,2,3,4-tetrahydro-1-(1H-1,2,4-triazol-1-ylmethyl)naphthalene-6-carbonitrile, (1R*,2R*)- and (1R*,2S*)-2-(4-fluorophenyl)-1,2,3,4-tetrahydro-1-(1H-imidazolylmethyl)naphthalene-6-carbonitrile, (1R*,2R*)- and (1R*,2S*)-2-(4-cyanophenyl)-1,2,3,4-tetrahydro-1-(1H-1,2,4-triazol-1- ylmethyl)naphthalene-2,6-dicarbonitrile, (1R*,2R*)- and (1R*,2S*)-2-(4-cyanophenyl)-1,2,3,4-tetrahydro-1-(1H-imidazol-1-ylmethyl)naphthalene-6-carbonitrile and (1R*,2S*)-2-(4-fluorophenyl)-1,2,3,4-tetrahydro-1-(5-methyl-1H-imidazolylmethyl)naphthalene-6-carbonitrile.

9. A pharmaceutical or veterinary composition which comprises an effective amount of a heterocyclic compound as claimed in claim 1 together with a pharmaceutically or veterinarily acceptable diluent or carrier.

10. A method of treating steroid hormone-dependent tumours, which comprises administering to a host in need of such treatment an effective amount of a heterocyclic compound as claimed in claim 1.

* * * * *